(12) United States Patent
Stockham

(10) Patent No.: US 7,459,569 B2
(45) Date of Patent: Dec. 2, 2008

(54) METHOD OF FORMING IRON HYDROXYPYRONE COMPOUNDS

(75) Inventor: Michael A. Stockham, Essex (GB)

(73) Assignee: Vitra Pharmaceuticals Limited, Essex (GB)

( * ) Notice: Subject to any disclaimer, the term of this patent is extended or adjusted under 35 U.S.C. 154(b) by 86 days.

(21) Appl. No.: 10/514,836

(22) PCT Filed: May 7, 2003

(86) PCT No.: PCT/GB03/01956

§ 371 (c)(1),
(2), (4) Date: Jul. 8, 2005

(87) PCT Pub. No.: WO03/097627

PCT Pub. Date: Nov. 27, 2003

(65) Prior Publication Data

US 2005/0250754 A1    Nov. 10, 2005

(30) Foreign Application Priority Data

May 18, 2002    (GB)    ................................. 0211500.4

(51) Int. Cl.
C07D 309/40    (2006.01)
(52) U.S. Cl. ...................... 549/210; 514/184
(58) Field of Classification Search ................ 514/184; 549/206, 210
See application file for complete search history.

(56) References Cited

U.S. PATENT DOCUMENTS

| | | | |
|---|---|---|---|
| 3,130,204 A | 4/1964 | Tate et al. | |
| 3,365,469 A | 1/1968 | Tate et al. | |
| 3,592,889 A | 7/1971 | Lindvall et al. | |
| 4,018,907 A | 4/1977 | Scarpellino | |
| 4,212,685 A * | 7/1980 | Tuttle | 148/244 |
| 4,279,936 A | 7/1981 | Jones et al. | |
| 4,550,101 A | 10/1985 | Hider et al. | |
| 4,575,502 A | 3/1986 | Hider et al. | |
| 4,585,780 A | 4/1986 | Hider et al. | |
| 4,587,240 A | 5/1986 | Hider et al. | |
| 4,650,793 A | 3/1987 | Hider et al. | |
| 4,665,064 A | 5/1987 | Hider et al. | |
| 4,666,927 A | 5/1987 | Hider et al. | |
| 4,834,983 A | 5/1989 | Hider et al. | |
| 4,840,958 A | 6/1989 | Hider et al. | |
| 4,861,767 A | 8/1989 | Hider et al. | |
| 4,866,052 A | 9/1989 | Hider et al. | |
| 4,912,118 A | 3/1990 | Hider et al. | |
| 5,028,411 A * | 7/1991 | Callingham et al. | 424/45 |
| 5,104,865 A | 4/1992 | Hider et al. | |
| 5,177,068 A | 1/1993 | Callingham et al. | |
| RE34,313 E | 7/1993 | Hider et al. | |
| 5,256,676 A | 10/1993 | Hider et al. | |
| 5,480,894 A | 1/1996 | Hider et al. | |
| RE35,948 E | 11/1998 | Hider et al. | |
| RE36,831 E | 8/2000 | Hider et al. | |
| 6,197,763 B1 | 3/2001 | Hepworth Thompson et al. | |
| 6,339,080 B1 * | 1/2002 | Stockham et al. | 514/184 |
| 6,635,631 B2 | 10/2003 | Stockham et al. | |

FOREIGN PATENT DOCUMENTS

| | | |
|---|---|---|
| EP | 0 107 458 B1 | 5/1984 |
| EP | 0 159 194 B1 | 10/1985 |
| EP | 0 159 917 B1 | 10/1985 |
| GB | 2 128 998 A | 5/1984 |
| GB | 2 157 686 A | 10/1985 |
| JP | 03 067 565 | 3/1991 |
| WO | WO 96/41627 | 12/1996 |
| WO | WO 98/16218 | 4/1998 |

OTHER PUBLICATIONS

Yoneda, Masahiko et al. (ca. abstract only).*
Bezkorovainy et al. (ca. abstract only).*
Ahmet, M.T., et al., "A Potential Iron Pharmaceutical Composition for the Treatment of Iron-deficiency Anaemia. The Crystal and Molecular Structure of *mer*-Tris-(3-hydroxy-2-methyl-4*H*-pyran-4-onato)iron(III)," *J. Chem. Soc. Dalton Trans.* 1159-1163, Royal Society of Chemistry (1988).
El-Jammal, A. and Templeton, D.M., "Reversed-phase high-performance liquid chromatography of non-transferrin-bound iron and some hydroxypyridone and hydroxypyrone chelators," *J. Chromatography B*. 658:121-127, Elsevier Science (1994).
Luca, C., et al., "The Amphionic Structure of 3-Hydroxy-2-methyl-4H-pyran-4-one and the Properties of its Complexes with Iron Ions," *Rev. Roum. Chim*. 38:123-130, Académie Roumaine (1993).
Rice-Evans, C. and Baysal, E., "Iron-mediated oxidative stress in erythrocytes," *Biochem. J.* 244:191-196, Portland Press on Behalf of The Biochemical Society (1987).
Seeberg, V.P., et al., "Hemoglobin Regeneration Following Oral Administration of Chelated Iron," *Science* 119:608-609, American Association for the Advancement of Science (1954).
Stefanović, A., et al., "On the Reaction of Iron(III) with Maltol," *Collection. Czechoslov. Chem. Commun*. 33:4198-4214, Nakladatelstvi Ceskoslovenski Akademie Ved (1968).
Dialog File 351, Accession No. 8624725, Derwent WPI English language abstract of Japanese Patent No. 03 067 565 (Document AL2).
English language abstract of Hoiman, J.M. and Dukanovic-Stefanovic, A.B., "Spectrophotometric study of the iron-meconic acid complexes," Glas. Hem. Drus., Beograd 31:311-324, (1966), Dialog File 399 (Chemical Abstracts) Accession No. 70:51157 CA, Chemical Abstracts Service (1970).

(Continued)

*Primary Examiner*—B. Dentz
*Assistant Examiner*—David E Gallis
(74) *Attorney, Agent, or Firm*—Sterne, Kessler, Goldstein & Fox PLLC

(57) ABSTRACT

A method of forming an iron hydroxypyrone compound comprising reacting an iron salt of a carboxylic acid and a hydroxypyrone in an aqueous solution at a pH greater than 7.

10 Claims, No Drawings

OTHER PUBLICATIONS

International Search Report for International Application No. PCT/GB96/01382, issued Jan. 30, 1997.
International Search Report for International Application No. PCT/GB01/04052, mailed Dec. 2, 2002.
International Search Report for International Application No. PCT/GB03/01956, mailed Aug. 21, 2003.
UK Patent Office Search Report for UK Patent Application No. 0211500.4, Nov. 6, 2002.

* cited by examiner

METHOD OF FORMING IRON HYDROXYPYRONE COMPOUNDS

CROSS-REFERENCE TO RELATED APPLICATIONS

This application is a National Stage of International Application No. PCT/GB03/01956, filed May 7, 2003.

The present invention relates to a method of forming iron hydroxypyrone compounds and to compositions obtainable by the method.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born. Moreover, in certain pathological conditions where there is blood loss, or where there is a mal-distribution of iron in the body, there may be a state of chronic anaemia. This is seen in diseases such as Crohn's disease, rheumatoid arthritis, certain haemolytic diseases and cancer.

Iron in the ferrous state ($Fe^{II}$) is a strong reducing agent and can also interact with, and damage, proteins, carbohydrates and lipids and can therefore be harmful to the body. It has been thought, therefore, that iron is best delivered to the body and kept in the body in the ferric state ($Fe^{III}$). However, it is difficult to do this because the poor solubility of acceptable ferric compounds causes their bioabsorption to be poor. The absorption rate of ferrous salts such as ferrous sulphate is typically 30% when given on an empty stomach but this causes unpleasant side effects particularly with chronic medication. When given with food, the absorption may fall to 1 to 3% of the administered dose. For some anaemias, a daily uptake of 30 milligrams of iron is required, and although a wide range of iron compounds is already marketed for the treatment of iron deficiency anaemia, the poor levels of iron uptake by the body from these compounds necessitates relatively high dosage levels. However, the administration of high doses of poorly absorbed iron complexes may cause siderosis of the gut wall and a variety of side effects such as stomach pains, nausea, vomiting, constipation and heavy black stools which can result in poor patient compliance with their treatment.

Neutral (i.e., charge balanced) ferric compounds comprising hydroxypyrones are of particular interest because they may be used in the treatment and/or prevention of iron-deficiency anaemia and may reduce and/or avoid some or all of the problems associated with previously used ferric complexes.

EP 0159194 describes neutral (i.e., charge balanced) ferric iron complexes comprising specified combinations of ligands selected from 3-hydroxypyrones, 3-hydroxypyridones and specific mono-carboxylic acids. The molar ratio of iron to ligand is 1:3. The complexes are described for use at relatively low dosage levels for ferric compounds, in the treatment of iron deficiency anaemia. In the body, these complexes are considered to be transferred into the gastrointestinal cell and then to dissociate to provide iron for absorption and transfer onto the body's natural uptake processes.

In order to produce neutral (i.e., charge balanced) ferric complexes, EP 0159194 teaches the reaction of an ethanolic solution of ferric chloride with a chloroform solution of a hydroxypyrone ligand followed by adjustment of the pH with solid sodium carbonate.

GB 2128998 teaches that a neutral (i.e., charge balanced) complex comprising maltol and iron in the ferric state in a stoichiometric ratio of 3:1 (maltol:iron) confers a therapeutic effect.

GB 2128998 and EP 0107458 both teach a method of preparation of neutral (i.e., charge balanced) iron (III) maltol complexes which involves mixing a solution of maltol in chloroform with a 1M solution of ferric chloride in ethanol to provide a 3:1 molar ratio of maltol:iron in the mixture. After 5 minutes at 20° C. a 10 molar excess of solid sodium carbonate is added to the solution and the mixture is stirred for 10 minutes. The mixture is then filtered and solvent evaporated to give the neutral complex containing maltol and the ferric cation in 3:1 proportion. Recrystallisation of the 3:1 complex from ethanol provides the pure neutral ferric complex.

The above process for producing neutral ferric complexes of hydroxypyrone has several drawbacks. The first of these is that the process requires the use of organic solvents. Organic solvents are expensive, toxic and flammable. Furthermore, the organic residues obtained as a result of the process have to be disposed of, which requires further expense and safety measures. In addition, the reaction is unpredictable because the sodium carbonate causes bubbles of carbon dioxide to form in the solution. As a result, there may be gum formation on the reaction vessel. This gum comprises ferric maltol but it also contains impurities such as ferric hydroxide, which mean that the product is not suitable for use as a pharmaceutical compound.

Previously, ferric chloride has always been used as the source of ferric iron in the synthesis of ferric trimaltol. Ferric chloride is an attractive starting material because it is cheap, stable and readily available. However, attempts to improve the synthesis of ferric trimaltol have been hindered by the fact that ferric chloride is most soluble at acid pH values while maltol is most soluble at high pH values.

U.S. Pat. No. 6,339,080 is concerned with the preparation of charged mono- and di- hydroxypyrone complexes of iron (III) with carboxylic acids as counterions. However, U.S. Pat. No. 6,339,080 also teaches that a precipitate of a neutral (i.e., charge balanced) 1:3 iron (III) hydroxypyrone complex may be formed as a side product during the preparation of a mono-maltol complex when it is buffered to pH 7 with morpholine propane sulphonate. The yield of the complex obtained by this method is, however, only about 10%, which is not acceptable for a commercial synthesis.

There remains a need for further methods of forming iron hydroxypyrone compounds, which methods avoid or reduce some or all of the above-mentioned problems associated with the known methods for producing neutral (i.e., charge balanced) ferric hydroxypyrone complexes. In particular, there is a need to avoid the use of organic solvents in the process, and/or to avoid previous impurities and/or to increase the yield of the ferric hydroxypyrone and/or to reduce the overall amount of solvent required for the reaction.

According to a first aspect of the present invention there is provided a method of forming an iron hydroxypyrone compound comprising reacting an iron salt of a carboxylic acid and a hydroxypyrone in an aqueous solution at a pH of greater than 7.

In a further aspect of the present invention there is provided an iron hydroxypyrone compound obtained by the method of the present invention.

In another aspect of the present invention there is provided a ferric salt of a $C_1$ to $C_6$ alkyl di- or tri-carboxylic acid, optionally substituted with at least one hydroxyl group, comprising one or more monovalent cations selected from sodium or potassium and mixtures thereof.

In a yet further aspect of the present invention, there is provided a composition comprising an iron hydroxypyrone compound and a non-ferric salt of a carboxylic acid.

The method of the present invention may provide an unexpected improvement in the yield of the iron hydroxypyrone compound. Thus, typical yields of iron hydroxypyrone compounds formed in the method of the present invention may be in the range of from 50% to 100% by moles of the theoretical maximum based on the starting iron species, more preferably 80% to 100%.

In addition, the method of the present invention may avoid the formation or ferric hydroxide, which is a typical and important impurity when using iron chloride as a starting material. Ferric hydroxide is insoluble and cannot be absorbed by the body.

Furthermore, the method of the invention has the further advantage that the composition that is obtained by the method can comprise simply the iron hydroxypyrone and a non-ferric salt of a carboxylic acid. Such compositions may be buffered, in vitro or in vivo, by virtue of the non-ferric salt of a carboxylic acid that is present in the iron composition as a by-product of the present method. The composition may therefore be used without further modification. Alternatively, an acid, such as the carboxylic acid which forms the anion of the non-ferric salt, may be added to increase the buffer capacity of the composition. As a further alternative, the iron hydroxypyrone may be purified from the composition.

This "self-buffering" feature may help to stabilise a neutral (i.e., charge balanced) ferric hydroxypyrone complex when the ferric complex is dissolved in aqueous solution. Buffering a solution of a neutral ferric complex may reduce the likelihood of disproportionation of the complex. As a result, buffering can reduce the potential for the formation of insoluble iron species. Insoluble iron species are undesirable because the iron in these species is not available for bioabsorption by the body and, as a result, higher doses of the ferric complex may have to be used in order to achieve the desired effect.

As the skilled person in the art will readily appreciate, carboxylic acid systems, such as, for example, acetic acid and acetate and citric acid and citrate are capable of buffering the pH in aqueous solutions and of therefore inhibiting a change of pH.

A further unexpected advantage of the present invention is that the solubility of the iron composition obtainable by the present method may be improved in aqueous solution. Without wishing to be bound by theory, the improvement in solubility is believed to be due to the presence in the composition of the non-ferric salt of a carboxylic acid, such as, for example sodium citrate.

The term "iron composition", as used herein, refers to compositions of the invention containing iron in the +2 or +3 oxidation state.

The method of the present invention may provide an iron composition in which the by-products of the reaction comprise a pharmaceutically acceptable excipient or carrier, such as, for example, sodium citrate. The product obtainable by the method of the present invention may therefore be used in medicine without the need for further purification steps. However, purification can be carried out, if desired.

The fact that purification may not be required in order for the iron compositions to be suitable for use is advantageous because purification is often time-consuming and may require expensive techniques, apparatus or reagents. Furthermore, purification may result in a reduction in the yield of the iron hydroxypyrone compound.

Furthermore, the pharmaceuticaly acceptable excipient that is a by-product of the present invention may be more palatable to a patient than, for example, sodium chloride, which is the by-product of methods starting from ferric chloride. Thus, for example, the combination of ferric trimaltol and sodium citrate has a slightly bitter caramel taste, which may be preferred to the salty taste of sodium chloride.

The present invention partly involves the recognition that iron salts of certain carboxylic acids are soluble in an aqueous solution at a pH greater than 7. Thus, the solubility of the iron salt of a carboxylic acid used in the invention in water may suitably range from 25 g/liter to 3000 g/liter at 20° C. at a pH greater than 7 (such as pH 10). Such solubility of the iron salt of a carboxylic acid was entirely unexpected and advantageous.

Thus, the solubility properties of the iron salt of a carboxylic acid may avoid the need for high dilution reactions i.e., reactions that are carried out using reagent concentrations of less than 0.1M. The method of the present invention may therefore reduce the amount of solvent to be evaporated compared to known methods, which is an important advantage for commercial synthesis.

It is understood that the term "iron hydroxypyrone compound" does not include mixed ligand complexes comprising both hydroxypyrone ligands and carboxylate ligands covalently bound to an iron ion.

The iron hydroxypyrone compounds formed by the method of the present invention are preferably neutral complexes comprising iron cations and hydroxypyrone anions.

By "neutral complex", it is intended to mean that the positive charge on the iron cation is balanced by the negative charge on the ligands in the complex. Therefore the total charge on the iron hydroxypyrone complex is zero. Because there is an internal balance of charges between the iron cation and the hydroxypyrone ligands, there is no need for any additional non-covalently bound anions, such as chloride, to balance any remaining charge on the iron cation.

The iron hydroxypyrone compound may suitably comprise iron in the ferrous ($Fe^{2+}$) or ferric ($Fe^{3+}$) oxidation states. Alternatively, the iron hydroxypyrone compound may comprise a mixture of iron in the ferrous and ferric oxidation states.

Preferably, the iron hydroxypyrone compound comprises iron in the ferric state.

When the iron is present in the ferric state, the neutral iron hydroxypyrone complex comprises hydroxypyrone and ferric iron in the stoichiometric ratio of 3:1 hydroxypyrone:ferric iron. The neutral complex of ferric iron and hydroxypyrone comprises three monobasic, bidentate hydroxypyrone ligands covalently bound to a ferric ion. The hydroxypyrone ligand is a bidentate ligand and is monobasic. The singly charged hydroxypyrone ligand contains an —$O^-$ group in place of the —OH group present in the neutral hydroxypyrone ligand.

The hydroxypyrone ligands in the iron hydroxypyrone compounds may be the same or different. In a preferred embodiment, all of the hydroxypyrone ligands are the same.

Advantageously, the iron hydroxypyrone compound may be completely or substantially free of charged ferric hydroxypyrone complexes and neutral mixed ligand ferric complexes comprising covalently bound carboxylate ligands.

By "charged ferric hydroxypyrone complexes", it is intended to mean ferric hydroxypyrone complexes in which the stoichiometric ratio of hydroxypyrone to ferric iron is 2:1 or 1:1 so that the charge on the ferric cation is not internally balanced by the charge on the hydroxypyrone ligand. The total charge on the complex may be +1 or +2 and at least one counterion, such as, for example, chloride will be required in order to balance the charge.

By "substantially free", it is meant that the charged ferric complexes or neutral mixed ligand ferric complexes comprising carboxylate ligands comprise less than 10% by weight of the total weight of the iron species in the final composition and preferably less than 5%.

Where the iron hydroxypyrone compound has one or more chiral centres, the iron hydroxypyrone compound may be obtained as either pure enantiomer or diastereoisomer, a racemic mixture or a mixture enriched in either enantiomer or diastereoisomer. The mixture of enantiomers or diastereoisomers may be separated and purified using any of the known methods in the art. However, the mixture of optical isomers is typically not separated and purified.

The iron salt of a carboxylic acid may comprise more than one different type of iron salt of a carboxylic acid. Preferably, however, the iron salt of a carboxylic acid comprises one type of iron salt comprising one type of carboxylic acid.

The iron salt of a carboxylic acid may suitably comprise iron in the ferrous ($Fe^{2+}$) or ferric ($Fe^{3+}$) oxidation states. Alternatively, the iron salt of a carboxylic acid may comprise a mixture of iron in the ferrous and ferric oxidation states.

The iron salt of a carboxylic acid preferably comprises iron in the ferric state. The iron hydroxypyrone compound in the invention is preferably ferric trimaltol.

Preferably, the iron ion and the carboxylic acid are present in the salt in a stoichiometric ratio of from 1:1 to 1:3. The stoichiometric ratio will be determined in part by the number of carboxyl groups that are present in the carboxylic acid.

In a further embodiment, the iron salt of a carboxylic acid may further comprise one or more monovalent cations, such as, for example, an alkali metal selected from sodium or potassium.

In a preferred embodiment, the iron salt of a carboxylic acid comprises two monovalent cations, more preferably one monovalent cation.

The iron salt of a carboxylic acid may comprise water, such as water of crystallisation. Alternatively, the iron salt may be substantially dry. By "substantially dry" it is intended to mean that the iron salt of a carboxylic acid comprises less than 5% by weight of water of the total weight of the iron salt of a carboxylic acid.

Advantageously, the physical form of the iron salt of a carboxylic acid may suitably be crystalline in nature or the iron salt may be in the form of a powder. Preferably, the iron salt of a carboxylic acid is chosen so as to be in the most soluble form in aqueous solution at a pH greater than 7. Conveniently, the iron salt may be triturated, optionally with at least one further iron salt, for example by grinding e.g., with a mortar and pestle, before being used in the method according to the present invention.

It is desirable that the ferric salt of a carboxylic acid has a solubility in the aqueous solution at a pH greater than 7 (such as pH 10) in the range of from 25 g/liter to 3000 g/liter at 20° C., more preferably the ferric salt of a carboxylic acid has a solubility in the range of from 500 g/liter to 1500 g/liter at 20° C.

The iron salt of a carboxylic acid suitable for use in the present invention may be obtained commercially from, for example, the Sigma-Aldrich Chemical Company. Alternatively, the iron salt of a carboxylic acid may be prepared and purified, if necessary, in accordance with any of the suitable methods known to those skilled in the art.

The carboxylic acids preferred for use in the present invention are $C_1$ to $C_{12}$ acids. The term "$C_1$ to $C_{12}$ acids" refers to carboxylic acids which comprise from 1 to 12 carbon atoms where this number excludes the carbon atom of any carboxylic acid groups.

The carboxylic acid may be saturated or when the number of carbon atoms is 2 or more the carboxylic acid may be unsaturated and comprise one or more carbon-carbon double bonds or carbon-carbon triple bonds. Where there is more than one carbon-carbon double bond or triple bond, these may be conjugated or unconjugated. The carboxylic acids may be linear or branched and comprise saturated carbocyclic rings, for example cyclopentyl or cyclohexyl, or partially or wholly unsaturated carbocyclic rings, for example phenyl.

Preferably, the iron salt of a carboxylic acid comprises a carboxylic acid that is a $C_1$ to $C_{12}$ acid, optionally substituted with at least one hydroxyl group, having more than one carboxylic acid group.

The number of carboxylic acid groups may be, for example, two, three, four or higher. Advantageously, the number of carboxylic acid groups is two or three. Where there are two or three carboxylic acid groups it is particularly preferred if each of the carboxylic acid groups is attached separately to directly adjacent carbon atoms (ie, —C($CO_2$H)—C($CO_2$H) or —C($CO_2$H)—C($CO_2$H)—C($CO_2$H)).

Advantageously, the carboxylic acid is a $C_2$ to $C_6$ acid, optionally substituted with at least one hydroxyl group, having two or three carboxylic acid groups.

Preferably, the number of hydroxyl group (i.e., —OH group) substituents is from 1 to 10, more preferably from 1 to 5.

According to the present invention, particularly suitable carboxylic acids are those having formula (A):

X—R$^1$—(CO$_2$H)  (A)

wherein X=OH, $CO_2$H or —$COCH_3$ and $R^1$ represents a $C_2$ to $C_{12}$, preferably $C_2$ to $C_6$, alkylene or alkenylene group, optionally substituted on the alkylene or alkenylene group by 1 to 6, preferably 1 or 2, carboxylic acid groups.

Preferred carboxylic acids include those having formula (B):

($CO_2$H)—R$^2$—($CO_2$H)  (B)

wherein $R^2$ represents a $C_2$ to $C_{12}$, preferably $C_2$ to $C_6$, alkylene or alkenylene group, optionally substituted on the alkylene or alkenylene group by 1 to 6, preferably 1 or 2, carboxylic acid groups.

An alkylene group is a divalent species with radicals separated by two or more (eg, from two to twelve) carbon atoms linked in a chain.

The alkylene groups may be branched or unbranched and may be open chain or, where they are $C_3$ to $C_{12}$ groups, cyclic. Unbranched open chain alkylene groups include, for example, methylene, ethylene, propylene, butylene, pentylene and hexylene. Branched open chain alkylene groups include, for example, 2-propylene, 2-butylene and 2-(2-methyl)propylene. Cyclic groups include cyclopropylene, cyclobutylene, cyclopentylene and cyclohexylene. Preferably, the alkylene groups are straight chain groups.

The alkylene groups may optionally be further substituted (i.e., in addition to the optional carboxylic acid substitutents) on the alkylene chain. Substitutents include one or more further $C_1$ to $C_{12}$ linear or branched alkyl groups and one or more further substituents, such as, for example, cyano, nitro, keto, hydroxyl, haloalkyl, —$CO_2$alkyl, halo, thiol (SH), thioether (eg, S-alkyl) and sulfonate. Hydroxyl substituents are particularly preferred.

The term "alkenylene" is defined similarly to the term "alkylene" but covers groups comprising a carbon-carbon double bond. An example of an alkenylene group is ethenylene, —HC=CH—. Alkenylene groups can be optionally substituted in the same way as alkylene groups. Where applicable, the compound comprising the carbon-carbon double bond may have either the (E) or (Z) geometry, and where there is more than one carbon-carbon double bond the compound may comprise all (E), all (Z) or a mixture of (E) and (Z) geometries.

The term "alkyl" is defined similarly to alkylene but includes monovalent linear or branched $C_1$ to $C_{12}$ groups. Linear groups include methyl, ethyl, propyl, butyl, pentyl and hexyl. Alkyl groups can be optionally substituted in the same way as alkylene groups.

It is particularly preferred that the carboxylic acid is selected from naturally occurring, physiologically acceptable carboxylic acids which are suitable for use in medicine.

The carboxylic acid is preferably selected from the group consisting of: citric acid, isocitric acid, succinic acid, fumaric acid, maleic acid, malonic acid, aconitic acid, glutaric acid, tartaric acid and mixtures thereof Other suitable carboxylic acids include lactic acid and gluconic acid.

If the carboxylic acid has one or more chiral centres, it may be used in the form of one enantiomer, may be enriched in one enantiomer or may be a racemic mixture.

It is particularly preferred if the carboxylic acid is citric acid, fumaric acid or gluconic acid and the iron salt of a carboxylic acid is ferric citrate, ferrous fumarate or ferrous gluconate.

When a ferrous salt, such as ferrous fumarate, is used in the method of the present invention, the ferrous ions may all be oxidised in solution and/or during reaction in solution to ferric ions. Thus, for example, ferrous fumarate may react with, for example, maltol in the method of the present invention to form ferric trimaltol along with sodium fumarate.

The iron salt of a carboxylic acid is preferably monosodium ferric citrate or disodium ferric citrate. More preferably, the iron salt of a carboxylic acid is sodium ferrous citrate or sodium ferric citrate.

Preferably, the hydroxypyrone used in the method of the present invention is a hydroxy-4-pyrone. It is particularly preferred if the hydroxy-4-pyrone is a 3-hydroxy-4-pyrone or a 3-hydroxy-4-pyrone in which one or more of the hydrogen atoms attached to the ring carbon atoms is replaced by an aliphatic hydrocarbon group having 1 to 6 carbon atoms.

Alternatively, the hydroxypyrone ligand may be a 5-hydroxypyrone, such as Kojic acid (5-hydroxy-2-(hydroxymethyl)-4-pyrone). In a further embodiment, the hydroxypyrone used in the method of the present invention may comprise mixtures of the hydroxypyrone ligands mentioned above.

The substituted 3-hydroxy-4-pyrones may comprise more than one type of aliphatic hydrocarbon group. However, it is generally preferred if there is substitution by one rather than two or three aliphatic hydrocarbon groups.

The term "aliphatic hydrocarbon group" is used herein to include both acyclic and cyclic groups that may be unsaturated or saturated, the acyclic groups having a branched chain or preferably a straight chain. Particularly preferred groups are those having from 1 to 4 carbon atoms, more preferably those having from 1 to 3 carbon atoms. Saturated aliphatic hydrocarbon groups are preferred, these being either cyclic groups such as the cycloalkyl groups cyclopropyl, and particularly cyclohexyl, or more preferably acyclic groups such as methyl, ethyl, n-propyl and isopropyl. Methyl and ethyl are particularly preferred.

Substitution at the 2- or 6-position is of particular interest, although, when the ring is substituted by the larger aliphatic hydrocarbon groups, there may be an advantage in avoiding substitution on a carbon atom alpha to the

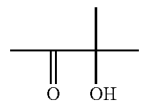

system. This system is involved in the formation of a complex with iron and the close proximity of one of the larger aliphatic hydrocarbons may lead to steric effects that inhibit complex formation.

Preferred hydroxypyrone ligands present in complexes according to the present invention have the formula (I), specific hydroxypyrones of particular interest have the formulae (II) and (III):

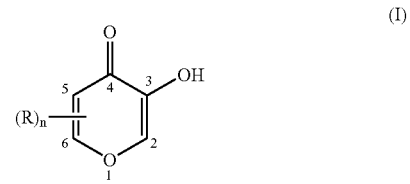

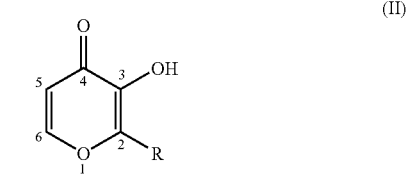

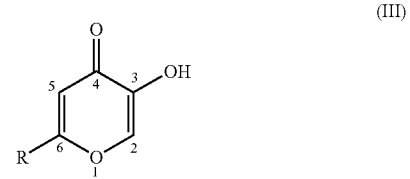

in which R is a cycloalkyl or alkyl group, for example, methyl, ethyl, n-propyl, isopropyl or butyl and n is 0, 1, 2 or 3 (the ring being unsubstituted by an alkyl group when n is 0).

Among these compounds, 3-hydroxy-2-methyl-4-pyrone (maltol; II, R=Me) is of most interest, whilst 3-hydroxy-4-pyrone (pyromeconic acid; I, n=0), 3-hydroxy-6-methyl-4-pyrone (isomaltol, III, R=Me) and particularly 2-ethyl-3-hydroxy-4-pyrone (ethylmaltol; II, R=Et) are also of especial interest. For convenience, the compound 3-hydroxy-2-methyl-4-pyrone is referred to herein as "maltol".

In a particularly preferred embodiment of the present invention the hydroxy-4-pyrone is selected from maltol, ethyl maltol and mixtures thereof. Maltol is most preferred and the iron hydroxypyrone compound of the invention is preferably ferric trimaltol.

Certain hydroxypyrones, such as maltol, are available commercially. With others, a convenient starting material in many instances consists of 3-hydroxy-4-pyrone, which is readily obtainable by the decarboxylation of 2,6-dicarboxy-3-hydroxy-4-pyrone (meconic acid). For example, 3-hydroxy-4-pyrone may be reacted with an aldehyde to insert a 1-hydroxyalkyl group at the 2-position, which group may then be reduced to produce a 2-allyl-3-hydroxy-4-pyrone. The preparation of 2-ethyl-3-hydroxy-4-pyrone, etc, by this route is described in U.S. application Ser. No. 310,141 (series of 1960) now abandoned. Other preparative methods are described by Spielman, Freifelder, J. Am. Chem. Soc. Vol. 69, Page 2908 (1947).

The skilled person will appreciate that these are not the only routes to these hydroxypyrone compounds and that various alternatives known in the art may equally be used.

According to the method of the present invention, the iron salt of a carboxylic acid and a hydroxypyrone are reacted in an aqueous solution at a pH greater than 7. This aqueous solution and all aqueous solutions discussed herein are preferably prepared using deionised water or distilled water. It is particularly preferred if the solutions are prepared using deionised water.

Furthermore, it is also preferred if the aqueous solutions used are substantially free of organic solvents such as for example, methanol, ethanol, acetone, chloroform, dichloromethane or ethyl acetate. By the term "substantially free" it is intended to mean that the aqueous solution comprises less than 10% (preferably less than 5%, more preferably less than 1%, most preferably, substantially 0%) of organic solvent by weight of the total aqueous solution.

The aqueous solution in which the reaction between the iron salt of a carboxylic acid and a hydroxypyrone takes place is preferably at a pH greater than 8, or preferably greater than 9, more preferably at a pH greater than 10. In a preferred embodiment, the pH of the solution is at a pH in the range of from 7.1 to 14, more preferably from 9.1 to 14, particularly preferably from 10 to 13.

Any of the pH values above may be achieved by using an aqueous solution comprising a suitable base at a certain concentration. By "suitable base" it is intended to mean any base that does not form a complex to an iron cation under the reaction conditions or interfere with the reaction between the iron salt of a carboxylic acid and a hydroxypyrone in any other way. The aqueous solution may comprise a single base or a mixture of two or more bases.

The pH may be measured using any of the means known to the skilled person in the art. This may include any of the commercially available electronic pH meters or universal indicator paper.

Preferably, the base is soluble in water at room temperature (20° C.) to the extent that it is able to provide the desired pH.

Examples of bases suitable for use in the present invention include bases selected from the group consisting of: alkali metal hydroxides, such as sodium and potassium hydroxide, and sodium or potassium carbonate.

Preferably the base is selected from the group consisting of: alkali metal hydroxides and mixtures thereof.

More preferably, the base is selected from sodium hydroxide or potassium hydroxide.

In a particularly preferred embodiment of the present invention, the base is selected from sodium hydroxide.

The above bases may be obtained from commercial sources, such as Sigma-Aldrich Company, or prepared according to any of the methods known to the person skilled in the art.

The concentration of base in the aqueous solution may suitably range from 0.1% to 50% by weight of the aqueous solution. Preferably, however, the concentration of base ranges from 10% to 30% by weight of the aqueous solution.

Preferably, the ratio of base to iron salt of a carboxylic acid may be stoichiometrically determined such that the final product comprises a neutral iron hydroxypyrone complex with a slight excess of maltol together with a carboxylate salt comprising the cation derived from the base. By "slight excess" it is meant that the excess of uncomplexed maltol ligand is between 1% and 10% by weight of the total maltol and maltol-containing species in the composition.

The stoichiometric ratio of base to iron salt of a carboxylic acid may be in the range of from 10:1 to 1:1, more preferably 10:1 to 1.5:1, most preferably 5:1 to 1:1.

Alternatively, any of the pH values disclosed above may be achieved using any suitable buffering system known to those skilled in the art.

According to the present method, the relative molar ratio of hydroxypyrone to iron salt of a carboxylic acid used in the reaction is preferably at least 3:1. Advantageously, the relative molar ratio may be in the range of 3:1 to 5:1. However, in a particularly preferred embodiment of the present invention, the molar ratio of hydroxypyrone ligand to iron salt of a carboxylic acid is 3.1:1 to 3.5:1.

The person skilled in the art will appreciate that pH and the solubility of particular iron hydroxypyrone compounds in aqueous solution will also determine the nature of the iron compounds formed. Therefore, the relative molar ratio of hydroxypyrone to iron salt of a carboxylic acid may be slightly less than 3:1 at higher values of pH (i.e., greater than 10) or with complexes that are less soluble in aqueous solutions in order to produce acceptable yields of iron hydroxypyrone compounds.

In a preferred embodiment of the present invention an aqueous solution at a pH specified above is prepared by adding an amount of base to water, preferably deionised or distilled water. The concentration of base will determine the pH value and the amount of base necessary to provide a particular pH value can be calculated accordingly.

The iron salt of a carboxylic acid or hydroxypyrone may be added to the aqueous solution at a pH specified above in a solid form.

Preferably, the iron salt of a carboxylic acid is added to the aqueous solution at a pH specified above in the form of a solid, preferably triturated. If necessary, further amounts of the aqueous solution at a pH specified above may be added in order to dissolve all of the salt.

In a preferred embodiment of the invention, the iron salt of a carboxylic acid is added in a solid form to an aqueous solution of a hydroxypyrone at a pH specified above. The solution may, alternatively, be added to the solid.

In some cases, a solution of the iron salt of a carboxylic acid in water by itself may have a pH greater than 7, so that adjustment of the pH using a base is unnecessary.

Alternatively, the iron salt of a carboxylic acid or hydroxypyrone may be added to the aqueous solution at a pH specified above in the form of one or more separate further aqueous solution(s) at a pH greater than 7.

A separate further aqueous solution comprising hydroxypyrone is preferably added to the aqueous solution at a pH specified above. Preferably, the further aqueous solution is at a pH greater than 7, more preferably greater than 9, particularly preferably greater than 10.

In any of the above embodiments, the iron salt of a carboxylic acid and hydroxypyrone may be triturated separately before being added to any aqueous solution.

The iron salt of a carboxylic acid may be added to the aqueous solution at a pH specified above at the same time, before, or after the hydroxypyrone. Preferably, the iron salt of a carboxylic acid is added before the hydroxypyrone. In this embodiment, it is preferred that all of the solid iron salt of a carboxylic acid is dissolved in the aqueous solution at a pH specified above, before the hydroxypyrone is added.

The method of the present invention may comprise mixing a solution of the iron salt of a carboxylic acid with a solution of the hydroxypyrone.

In a particularly preferred embodiment of the present method, the iron salt of a carboxylic acid and hydroxypyrone are added to separate volumes of the aqueous solution at a pH specified above in a solid form. These volumes are then combined once the solid has dissolved. To dissolve the solid may optionally require heating and/or stirring and/or the addition of further amounts of the aqueous solution at a pH specified above. The solution of iron salt may be added to the solution of hydroxypyrone and vice versa.

In a further preferred embodiment, the iron salt of a carboxylic acid may be dissolved, optionally with stirring and/or heating, in water, preferably distilled, whose pH has not been adjusted using a base. This solution may be combined with an aqueous solution of a hydroxypyrone at a pH greater than 7, such as 10. The iron hydroxypyrone compound formed may be isolated as a precipitate and optionally dried at, for example 80° C., or alternatively the solvent of the reaction mixture may be removed by, for example, evaporation and the resulting powder dried to a constant weight.

The concentration of the iron salt of a carboxylic acid or the hydroxypyrone in the aqueous solution at a pH specified above may be in the range of from 0.1 to 20 mol/liter, preferably from 1 to 15 mol/liter, more preferably from 4 to 12 mol/liter.

If necessary, the pH of the aqueous solution at a pH specified above may be adjusted, after addition of the iron salt of a carboxylic acid and/or the hydroxypyrone, by adding further amounts of base such that the pH is at a pH greater than 7.

Without wishing to be bound by theory it is believed that in certain embodiments of the present invention the iron salt of a carboxylic acid, such as, for example, ferric citrate, may react exothermically in situ with a base, such as, for example, sodium hydroxide, in order to produce a solution of a further iron salt, such as for example, sodium ferric citrate, which reacts with the hydroxypyrone.

In a preferred embodiment of the present invention, the iron salt of a carboxylic acid and the hydroxypyrone ligand are dissolved in the aqueous solution.

The method of the invention is preferably carried out at a temperature of from 0° C. to 80° C., more preferably from 10° C. to 40° C., for a period of from 1 minute to 60 hours, more preferably from 30 hours to 50 hours, particularly preferably from 40 to 50 hours.

The reaction may suitably be carried out under atmospheric pressure, preferably with stirring of the reaction mixture. The reaction may be conducted under an inert atmosphere of, for example, argon or nitrogen.

If light sensitive materials are used the reaction may also be carried out in the absence of direct sunlight, or in the dark, and solutions of reagents may be kept in the dark in order to avoid substantial decomposition of the reagents.

The solubility of the iron hydroxypyrone compound in the reaction mixture may be such that it precipitates from solution. In one embodiment, the solubility of the iron compound may be from 0.01% to 5% w/v at 20° C. and at a pH above 7 (such as 10). Depending on the volume of supernatant liquid, from 40% to 98%, preferably 70% to 90%, by moles of the theoretical maximum of the iron compound may precipitate. This may be isolated by separating the precipitated solid from the liquid using techniques well known in the art, such as filtration and decantation.

The precipitation of the iron hydroxypyrone compound may be enhanced by cooling the reaction mixture, using, for example, a cold water or ice and cold water bath, to cool the solution to a temperature of from −10° C. to +10° C.

The supernatant liquid may include, for example, non-ferric carboxylate salts, such as sodium or potassium carboxylate salts, up to 100% by moles of the theoretical maximum, and iron hydroxypyrone compounds with differing molar ratios of iron:hydroxypyrone, such as 1:1 or 1:2. The supernatant liquid may optionally be separated from any solid by any suitable method, for example filtration, and dried at for example 80° C., preferably to a constant weight.

The iron hydroxypyrone compounds are optionally dried, preferably at a temperature of 80° C., and may be purified further and isolated as substantially pure products according to the methods known in the art such as, for example, recrystallisation. Recrystallisation may be carried out using solvents such as, for example, water, an alcohol such as ethanol, aqueous alcoholic mixtures, or mixtures of aqueous solvent mixtures comprising an ether such as, for example, diethyl ether or tetrahydrofuran.

It is preferred, however, if recrystallisation is avoided where this will lead to a significant reduction (i.e., greater than 10% by moles of the theoretical maximum based on the starting iron species) in the yield of the iron hydroxypyrone compound.

Alternatively, the reaction medium may be evaporated to dryness at a temperature that does not cause substantial decomposition of the products in order to produce a material that may be powdered and dried to a constant weight.

The evaporation and drying may be carried out at a temperature of from 40° C. to 120° C., more preferably from 60° C. to 80° C. The evaporation may also be carried out under reduced pressure, using, for example, a rotary evaporator or an oven which is capable of being placed under vacuum.

In a further aspect of the present invention, there is provided an iron hydroxypyrone compound obtained by the method of the present invention as described in any one of the above embodiments. Preferably, this is ferric trimaltol.

In another aspect of the present invention, there is provided a ferric salt of a $C_1$ to $C_6$ alkyl di- or tri-carboxylic acid, optionally substituted with at least one hydroxyl group, comprising one or more monovalent cations selected from sodium or potassium and mixtures thereof.

Preferably the stoichiometric ratio of monovalent cation to ferric ion in the above salt is in the range of from 3:1 to 0.5:1, more preferably from 2:1 to 1:1.

The ferric salt of carboxylic acid according to the above aspect of the present invention may be an intermediate in the reaction that leads to the iron hydroxypyrone compound of the present invention. Alternatively, the ferric salt of a carboxylic acid may be prepared and isolated and later used as a starting material for the method of the invention.

The above ferric salt may be prepared by the reaction of an aqueous solution of any base as described herein, preferably sodium or potassium hydroxide, with a different iron salt of a carboxylic acid, such as ferric citrate. The product may be isolated according to any of the known methods of the art for preparing ferric salts.

The number of monovalent ions contained in the above ferric salt of a carboxylic acid may be determined by varying the amount of base that is reacted with the different ferric salt of a carboxylic acid. Thus, for example, when the ferric salt is reacted with one equivalent of sodium hydroxide, the product may be the monosodium ferric salt. However, when two equivalents of sodium hydroxide are reacted with the ferric salt, the product may be the disodium ferric salt.

In a preferred embodiment of the present invention, the iron salt of a carboxylic acid is monosodium ferric citrate or disodium ferric citrate.

In a yet further aspect there is provided a composition comprising an iron hydroxypyrone compound and a non-ferric salt of a carboxylic acid. This composition may be obtained by the method of the present invention, or in other ways known to the skilled person such as simple mixing of the compound and the salt.

By the term "non-ferric" it is intended to include salts which comprise monovalent cations such as, for example, sodium, potassium and mixtures thereof.

The non-ferric salt of a carboxylic acid may be a by-product of the reaction by which the iron hydroxypyrone compound of the present invention is obtained or it may be added to an iron hydroxypyrone compound obtained by the method of the present invention.

It is preferred that the non-ferric salt of a carboxylic acid is pharmaceutically acceptable.

Advantageously, the molar ratio of iron hydroxypyrone compound to non-ferric salt of a carboxylic acid is in the range of from 100:1 to 1:100.

In an alternative embodiment, the molar ratio of iron hydroxypyrone compound to non-ferric salt of a carboxylic acid may be in the range of from 10:1 to 1:10, preferably, 5:1 to 1:5, more preferably from 2:1 to 1:2.

It is particularly preferred if the iron hydroxypyrone compound is ferric trimaltol and the non-ferric salt of a carboxylic acid is sodium citrate.

In a further aspect, the present invention relates to a pharmaceutical composition comprising the iron hydroxypyrone obtained by the method of the present invention, together with a pharmaceutically acceptable diluent or carrier.

The compositions of the present invention may further comprise one or more carboxylic acids. The carboxylic acid may correspond to the acid that is present as an acid counter-anion in the non-ferric salt in the composition or may be a different acid. Preferably the acid is the same as the acid from which the acid counterion in the non-ferric salt is derived. The acid may be selected from any of the carboxylic acids described herein and is preferably pharmaceutically acceptable and suitable for use in medicine.

The acid may be added in order to optimize the buffering efficiency of the iron compositions of the present invention in aqueous solution and/or in vivo.

Preferably, the molar ratio of carboxylic acid to non-ferric salt of a carboxylic acid in the composition of the invention is in the range of from 30:1 to 1:30, more preferably from 10:1 to 1:10.

By "pharmaceutically acceptable" we include the normal meaning that the carriers must be "acceptable" in the sense of being compatible with the active ingredient (the iron hydroxypyrone compound) and not deleterious to the recipients thereof.

The composition may be in the form of a solid or liquid. Suitable solid diluents and carriers include starch, dextrin and magnesium stearate. Stabilizing and suspending agents such as methylcellulose and povidone and other tableting agents such as lactose and flow aids such as Aerosil 2000™ may also be used.

Particularly useful diluents and carriers are wetting agents or surfactants, preferably non-ionic or ionic surfactants. Examples of suitable non-ionic surfactants include polyoxyl-10-oleyl ether and polysorbates. An example of a suitable ionic surfactant is sodium lauryl sulfate.

Liquid carriers should be sterile and pyrogen free: examples are saline and water.

In a particularly preferred embodiment of the present invention, the carrier comprises a by-product of the present invention and therefore there is no need for any further purification of the product obtained by the present method for use in medicine.

The iron hydroxypyrone compounds of the present invention provide particular advantages in relation to the formulation of iron complexes. Liquid formulations of the iron compounds are particularly suitable for oral and parenteral administration. In such applications, the solubility of some known iron complexes is unsatisfactory.

The iron hydroxypyrone compounds may be formulated with a physiologically acceptable diluent or carrier for use as pharmaceuticals for veterinary or human use in a variety of ways. However, compositions in which the diluent or carrier is other than a non-sterile solution in water and/or an organic solvent are generally preferred. Thus, the iron complexes may be applied as an aqueous, oily or emulsified composition incorporating a liquid diluent, which will, however, most usually be employed for parenteral administration and therefore may conveniently be sterile and pyrogen free. One form of composition of particular interest thus has the form of a sterile, injectable solution. Oral administration is, however, more generally to be preferred for the treatment of iron deficiency anaemia in humans, and the compositions of the present invention may be given by that route.

For oral administration in humans it is more usual to use compositions incorporating a solid carrier, for example, starch, lactose, dextrin or magnesium stearate. Such solid compositions may conveniently be shaped, for example in the form of tablets, capsules (including spansules), etc. However, liquid preparations are especially useful for oral administration to patients who have difficulty in swallowing solid forms. Such difficulties are common in patients suffering from anaemias associated with arthritis.

Other forms of administration than by injection or through the oral route may also be considered, for example the use of suppositories.

More than one iron hydroxypyrone compound obtained by the method of the present invention may be contained in a pharmaceutical composition and other active compounds may also be included. Typical additives include compounds having the ability to facilitate the treatment of anaemia, such as folio acid. A zinc source may also be included.

Preferably the above compositions are suitable for use in medicine.

The compositions of the present invention are particularly useful for serious anaemias arising from bleeding disorders, particularly of the gastrointestinal tract. Many of the patients with such disorders are intolerant of standard ferrous anti-anaemia compounds. Some ferrous preparations are contra-indicated in such conditions. Furthermore, patients who may need blood transfusions or in-patient treatment with intravenous injections can be treated on an outpatient basis saving substantial costs of treatment.

The pharmaceutical compositions may be used in a method for the treatment of a patient to effect an increase in the levels of iron in the patient's bloodstream which comprises administering to said patient an effective amount of an iron hydroxypyrone compound as defined previously.

The iron hydroxypyrone compounds obtained by the method of the present invention may also be used in the dry method preparation of the charged iron hydroxypyrone complexes disclosed in U.S. Pat. No. 6,339,080.

The following examples are intended to be illustrative of the present invention which is not to be considered to be limited thereto.

All percentages are percentages by weight unless indicated otherwise.

EXAMPLES

Example 1

Synthesis of Ferric Trimaltol Using Ferric Citrate

NaOH (12 g, 0.3 moles) is dissolved in water (50 ml) to form a sodium hydroxide solution. 20 ml of the sodium hydroxide solution is placed in a separate vessel.

Ferric citrate (30 g, 0.11 moles) is slowly added to the sodium hydroxide solution in the separate vessel at room temperature with gentle stirring. Further portions of the sodium hydroxide solution are added to the solution of ferric citrate, as necessary, in order to ensure that all of the ferric citrate is dissolved.

Maltol (49 g, 0.39 moles) is added to the remaining volume of sodium hydroxide solution and dissolved. The pH of the maltol solution is 11.6.

The ferric citrate solution is slowly added to the maltol solution with gentle stirring. A deep red precipitate forms; the supernatant is a deep red color.

The solution is slowly evaporated to dryness at 60 to 80° C. until the material is suitable for powdering. The material is powdered and the powder is then dried to a constant weight.

The yield of the final product is 87 g.

The final product comprises ferric trimaltol and sodium citrate. The product was assayed, using elemental analysis, for iron and sodium content. The iron content is 7.89% (theoretical 7.8%) and the sodium content is 13.45%.

The pH of a solution of the final product in water was measured. The pH of a 1% solution of the product by total weight of aqueous solution is 9.9 at 20° C.

Example 2

Synthesis of Ferric Trimaltol Using Ferrous Fumarate

NaOH (40 g, 1 mole) is dissolved in water (100 ml) to form a sodium hydroxide solution. The pH of the solution is approximately 13.0.

Ferrous fumarate (170 g, 1 mole) is slowly added to the sodium hydroxide solution at room temperature with gentle stirring.

Maltol (408 g, 3.23 moles) is added to a separate volume of sodium hydroxide (40 g, 1 mole) dissolved in water (100 ml) and dissolved. The pH of the solution is approximately 11.

The ferrous fumarate solution is slowly added to the maltol solution with gentle stirring. A deep red precipitate forms; the supernatant is a deep red color.

The solution is slowly evaporated to dryness at 60 to 80° C. until the material is suitable for powdering. The material is powdered and the powder is then dried to a constant weight.

The yield of the final product is 615 g.

The final product comprises ferric trimaltol and sodium fumarate.

Example 3

Synthesis of Ferric Trimaltol Using Sodium Carbonate to Vary pH

Sodium carbonate (2.5 g) is dissolved in 10 ml of distilled water at room temperature. The pH of the solution is 11.6. Maltol (9.6 g—three molar equivalents of sodium carbonate) is added to the sodium carbonate solution to give a cream colored solution having a pH of 10.0.

A stoichiometric amount of ferric citrate (5 g, allowing for a small excess of maltol) in an aqueous solution of sodium hydroxide (1 g in 5 ml of distilled water) is added slowly to the solution of maltol. The pH of the combined solutions is about 9. A red precipitate appears which is separated by decantation and dried at 80° C. in an oven.

The red precipitate is ferric trimaltol, as confirmed by UV-Vis spectrometry.

Example 4

Synthesis of Ferric Trimaltol Using Ferrous Gluconate

Potassium hydroxide (5.5 g) is dissolved in 50 ml of distilled water at room temperature. To 25 ml of this solution, maltol (16.5 g, 0.13 moles) is added and gently heated to form a clear solution.

To the other 25 ml aliquot of the potassium hydroxide solution ferrous gluconate (22.5 g) is added. This is gently heated to form a dark green saturated solution. The ferrous gluconate solution is added to the maltol solution and immediately a color change to dark brown is noted.

On cooling, a deep brown precipitate forms (which is ferric trimaltol). The supernatant is a deep brown solution containing ferric trimaltol and potassium gluconate. The precipitate and the supernatant are dried separately at 80° C. in an oven. The ferric trimaltol is a deep red brown powder with a characteristic caramel odour and UV-vis spectrum in aqueous solution.

Example 5

Synthesis of Ferric Trimaltol Using Solid Ferrous Gluconate

Example 4 was repeated with the modification that the maltol is added to all of the 50 ml solution of potassium hydroxide and then solid ferrous gluconate is added directly to the maltol solution. This method gives similar end products to Example 4.

Example 6

Synthesis of Ferric Trimaltol Using Sodium Ferrous Citrate

A 20% solution w/v of sodium ferrous citrate in distilled water is prepared from 7.5 g of sodium ferrous citrate in 37.5 ml of water. The solution of sodium ferrous citrate is dark green with an iron content of about 20%.

A solution of maltol (containing 10 g/50 ml) in 20% sodium hydroxide is added to the solution of sodium ferrous citrate. A characteristic deep red/brown iron complex of ferric trimaltol is formed.

Example 7

Synthesis of Ferric Trimaltol Using Solid Sodium Ferrous Citrate

Example 6 was repeated using the same amounts and concentrations of components but the method is varied in that solid sodium ferrous citrate (7.5 g) is added directly to the maltol solution (containing 10 g of maltol in 50 ml). Ferric trimaltol is formed using this alternative method.

Example 8

Synthesis of Ferric Trimaltol Using Sodium Ferric Citrate

A 20% solution w/v of sodium ferric citrate in distilled water is prepared from 7.5 g of sodium ferric citrate in 37.5 ml of water. The solution of sodium ferric citrate is dark brown with an iron content of about 20%.

A solution of maltol (containing 10 g/50 ml) in 20% sodium hydroxide is added to the solution of sodium ferric citrate. A characteristic deep red/brown iron complex of ferric trimaltol is formed.

Example 9

Example 8 was repeated using the same amounts and concentrations of components but the method is varied in that solid sodium ferric citrate (7.5 g) is added directly to the maltol solution (containing 10 g of maltol in 50 ml). Ferric trimaltol is formed using this alternative method.

If any of Examples 3 to 9 are repeated using maltol in a neutral or acidic aqueous medium, such as for example in buffered citric acid, brown/black impurities appear and insoluble fractions are formed probably of ferric hydroxide) and the UV-vis spectra of the solutions are not correct. In particular, there is a peak shift towards 510 nm indicating the formation of mono or dimaltol complexes or compounds.

Example 10

The following is an example of a pharmaceutical composition of the present invention for use in a capsule.

| Component | Amount |
| --- | --- |
| Ferric trimaltol | 236 mg |
| Sodium citrate | 150 mg |
| Citric acid | 50 mg |
| Sodium lauryl sulfate | 2 mg |
| Lactose | q.v. |

The invention claimed is:

1. A method of forming an iron hydroxypyrone compound which is a ferric hydroxypyrone complex comprising hydroxypyrone and ferric iron in the stoichiometric ratio of 3:1 hydroxypyrone: ferric iron, which comprises the step of reacting one or more iron salt of a carboxylic acid and one or more hydroxypyrone in an aqueous solution at a pH greater than 7, wherein the aqueous solution comprises one or more base selected from the group consisting of alkali metal hydroxides, sodium or potassium carbonate and mixtures thereof, wherein the carboxylic acid is selected from the group consisting of citric acid, isocitric acid, succinic acid, fumaric acid, maleic acid, malonic acid, aconitic acid, glutaric acid, tartaric acid, gluconic acid, lactic acid, and mixtures thereof, wherein the hydroxypyrone is selected from the group consisting of maltol or ethyl maltol, and mixtures thereof; and wherein the concentration of the base is from 1 to 50% by weight of the aqueous solution.

2. The method according to claim 1, wherein the pH of the aqueous solution is greater than 9.

3. The method according to claim 1, wherein the aqueous solution comprises one or more base selected from the group consisting of: alkali metal hydroxides and mixtures thereof.

4. The method according to claim 3, wherein the base is sodium hydroxide.

5. The method according to claim 1, wherein the molar ratio of hydroxypyrone to the iron salt is at least 3:1.

6. The method according to claim 1, wherein the one or more iron salt of a carboxylic acid and the one or more hydroxypyrone are dissolved in the aqueous solution.

7. The method according to claim 1, wherein the iron hydroxypyrone compound is ferric trimaltol.

8. The method according to claim 1, wherein the one or more iron salt of a carboxylic acid further comprises one or more monovalent cations selected from sodium or potassium.

9. A method of forming an iron hydroxypyrone compound which is a ferric hydroxypyrone complex comprising hydroxypyrone and ferric iron in the stoichiometric ratio of 3:1 hydroxypyrone: ferric iron, which comprises the step of adding one or more iron salt of a carboxylic acid in a solid form to a solution of one or more hydroxypyrone in an aqueous solution at a pH greater than 7, wherein the aqueous solution comprises one or more base selected from the group consisting of alkali metal hydroxides, sodium or potassium carbonate and mixtures thereof, wherein the carboxylic acid is selected from the group consisting of citric acid, isocitric acid, succinic acid, fumaric acid, maleic acid, malonic acid, aconitic acid, glutaric acid, tartaric acid, gluconic acid, lactic acid, and mixtures thereof, wherein the hydroxypyrone is selected from the group consisting of maltol or ethyl maltol, and mixtures thereof; and wherein the method comprises the step of adding the one or more iron salt of a carboxylic acid in a solid form to a solution of the one or more hydroxypyrone.

10. A method of forming an iron hydroxypyrone compound which is a ferric hydroxypyrone complex comprising hydroxypyrone and ferric iron in the stoichiometric ratio of 3:1 hydroxypyrone: ferric iron, which comprises the step of mixing a solution of one or more iron salt of a carboxylic acid with a solution of one or more hydroxypyrone in an aqueous solution at a pH greater than 7, wherein the aqueous solution comprises one or more base selected from the group consisting of alkali metal hydroxides, sodium or potassium carbonate and mixtures thereof, wherein the carboxylic acid is selected from the group consisting of citric acid, isocitric acid, succinic acid, fumaric acid, maleic acid, malonic acid, aconitic acid, glutaric acid, tartaric acid, gluconic acid, lactic acid, and mixtures thereof, wherein the hydroxypyrone is selected from the group consisting of maltol or ethyl maltol, and mixtures thereof; and wherein the method comprises the step of mixing a solution of the one or more iron salt of a carboxylic acid with a solution of the one or more hydroxypyrone.

* * * * *